United States Patent [19]

Craft

[11] Patent Number: 5,697,117
[45] Date of Patent: Dec. 16, 1997

[54] BRUSH HEAD ASSEMBLY FOR MOTOR POWERED TOOTHBRUSH

[75] Inventor: Adam B. Craft, Fort Collins, Colo.

[73] Assignee: Teledyne Industries, Inc., Fort Collins, Colo.

[21] Appl. No.: 592,043

[22] Filed: Jan. 26, 1996

[51] Int. Cl.⁶ .................... A61C 17/34; A46B 13/02
[52] U.S. Cl. ........................... 15/22.1; 15/21.1
[58] Field of Search ............... 15/21.1, 22.1, 15/22.2, 97.1; 173/162.1, 162.2, DIG. 2; 310/47; 601/93, 95

[56] References Cited

U.S. PATENT DOCUMENTS

| | | |
|---|---|---|
| 2,044,863 | 6/1936 | Sticht . |
| 2,158,738 | 5/1939 | Baker et al. . |
| 2,206,726 | 7/1940 | Lasater . |
| 2,875,458 | 3/1959 | Tsuda . |
| 2,917,758 | 12/1959 | Held et al. . |
| 3,104,405 | 9/1963 | Perrinjaquet . |
| 3,535,726 | 10/1970 | Sawyer . |
| 4,353,141 | 10/1982 | Teague, Jr. et al. ............ 15/22.1 |
| 4,432,729 | 2/1984 | Fattaleh ................. 15/22.1 |
| 4,698,869 | 10/1987 | Mierau et al. . |
| 4,991,249 | 2/1991 | Suroff . |
| 5,072,477 | 12/1991 | Pai ........................... 15/22.1 |
| 5,253,382 | 10/1993 | Beny . |
| 5,289,604 | 3/1994 | Kressner ................... 15/22.1 |
| 5,404,608 | 4/1995 | Hommann ................. 15/22.1 |
| 5,406,664 | 4/1995 | Hukuba ..................... 15/22.1 |

FOREIGN PATENT DOCUMENTS 1171337  1/1959  France .

*Primary Examiner*—Terrence Till
*Attorney, Agent, or Firm*—Holland & Hart LLP

[57] ABSTRACT

A brush-head assembly for a motor driven toothbrush including an elongated handle housing a motor with a primary drive shaft extending outwardly from one end of the handle, said assembly comprising a housing sleeve attachable at one end to said handle, said sleeve having a second end defining an inner cylindrical bearing surface and an annular end surface, a brush head including a shaft journaled in said second sleeve end and defining an outer cylindrical bearing surface juxtaposed with said inner cylindrical bearing surface and an annular shoulder juxtaposed with said annular end surface of said sleeve, and a soft resilient annular bushing positioned between said brush head shoulder and said sleeve end surface.

13 Claims, 4 Drawing Sheets

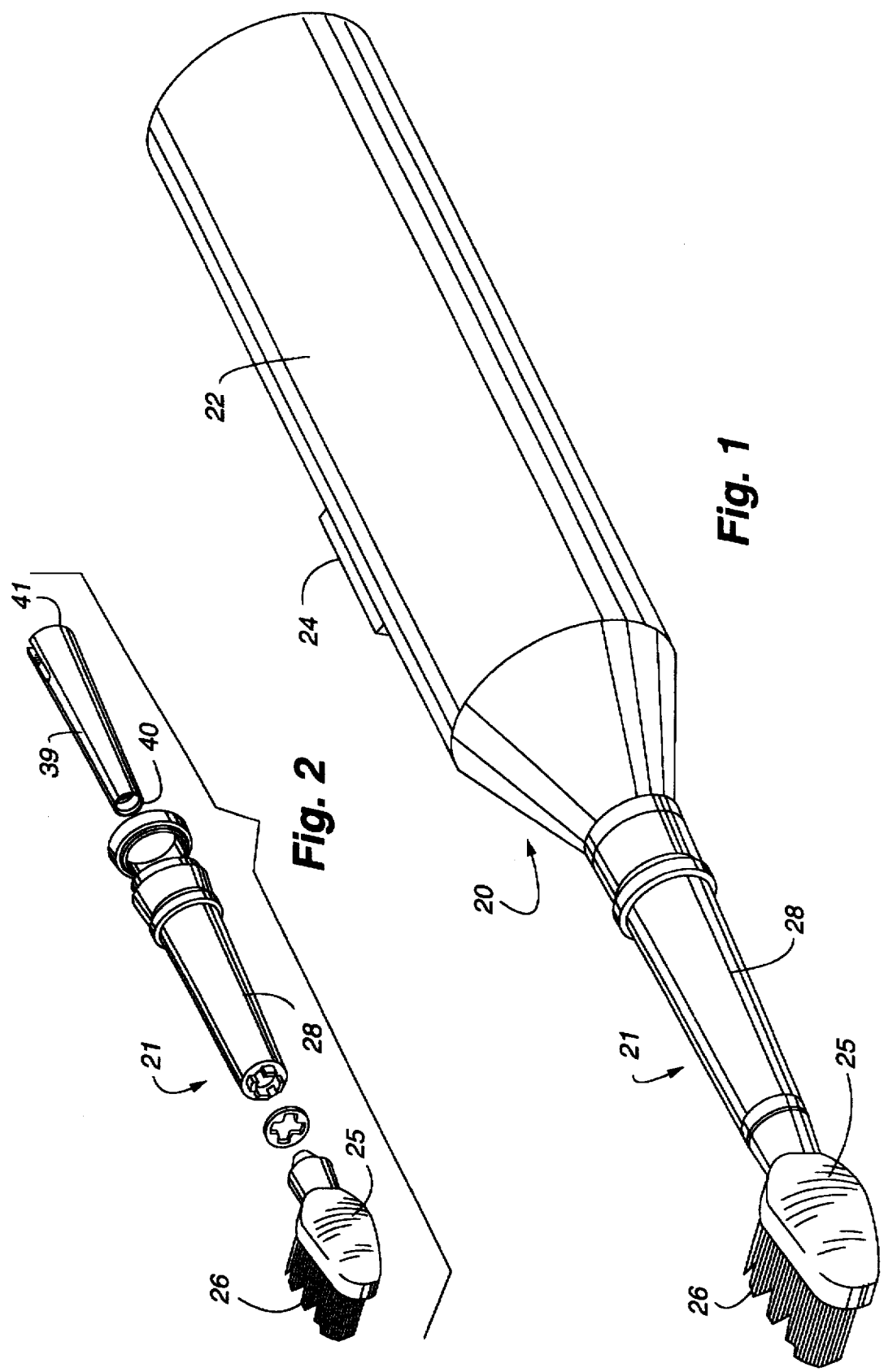

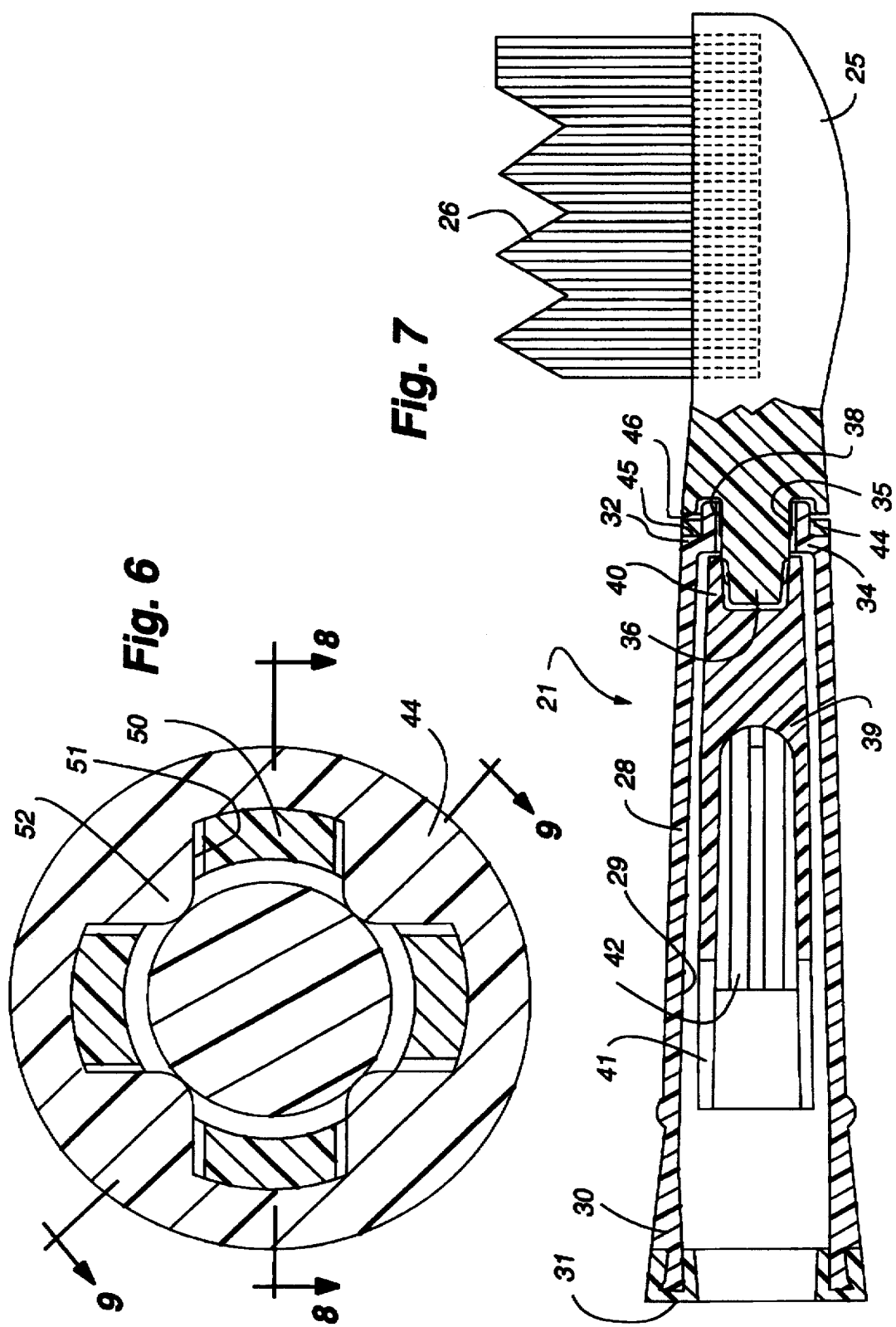

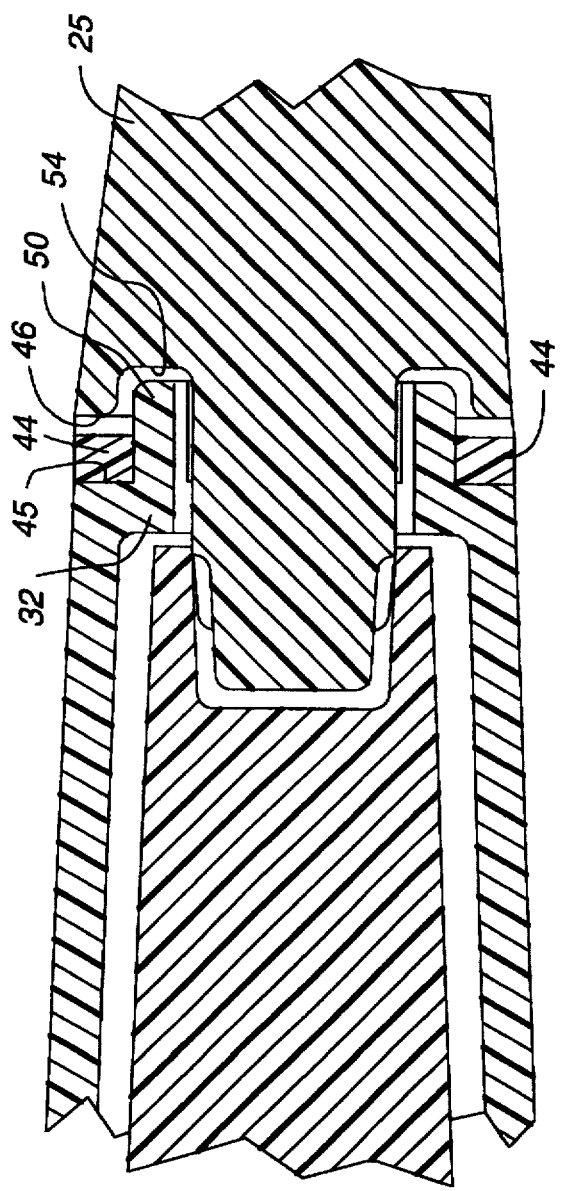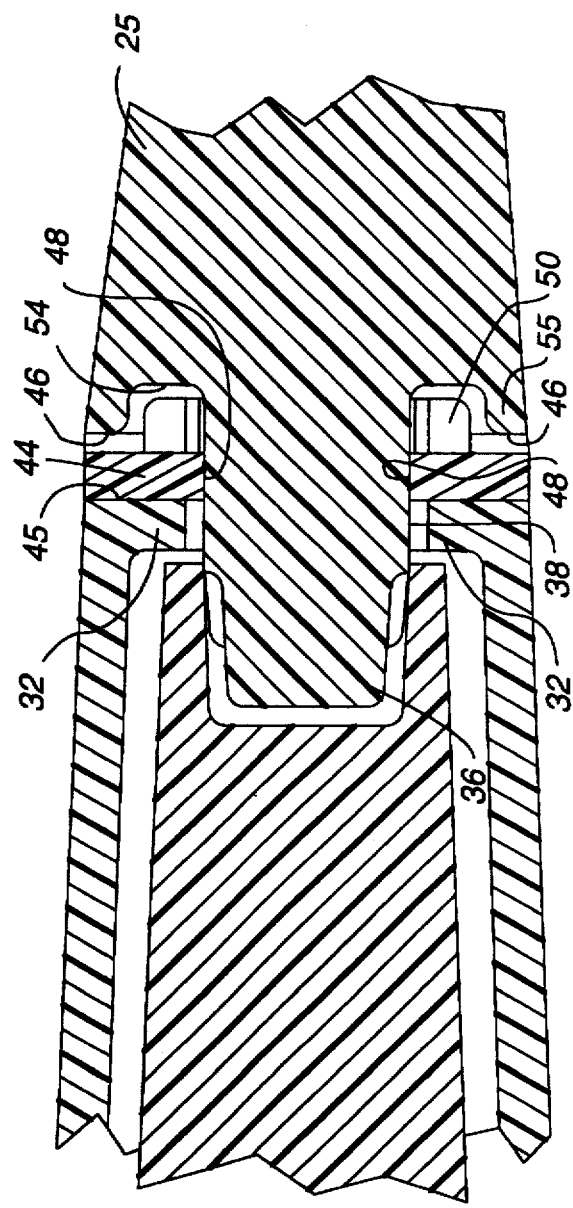

BRUSH HEAD ASSEMBLY FOR MOTOR POWERED TOOTHBRUSH

BACKGROUND OF THE INVENTION

1. Field of the Invention

This invention relates to motor powered toothbrushes, and more particularly to brush head assemblies therefor.

2. Description of the Prior Art

A motor powered toothbrush is described in detail in application Ser. No. 08/254,309 now U.S. Pat. No. 5,613,259, filed Jun. 6, 1994, for "High Frequency Electric Toothbrush" and assigned to the same assignee as the present application. Such a toothbrush includes a handle housing an electrically powered drive motor with a drive shaft extending outwardly from one end of the handle, and a removable brush head assembly attachable to the housing in driving engagement with the drive shaft. The brush head assembly includes a tapered housing sleeve journaling a tapered brush head drive shaft releasably splined at one end to the motor drive shaft and secured or bonded at its other end to a brush head for oscillating the brush head and bristles relative to the housing and handle.

OBJECTS OF THE INVENTION

The principal object of the present invention is to provide an improved brush head assembly for motor powered toothbrushes.

Another object of the present invention is to provide an improved brush head of the foregoing character that operates quietly and at a substantially reduced vibratory noise level without damping of the oscillation thereof.

A further object of the invention is to provide a brush head assembly of the foregoing character which operates at a substantially reduced noise level, particularly when the motor is on and the brush head is oscillating but the toothbrush is not applied against the user's teeth.

SUMMARY OF THE INVENTION

In accordance with the foregoing objects, the present invention is embodied in an improved minimum vibration and noise brush head assembly for a motor driven toothbrush. The toothbrush includes an elongated handle housing a motor with a primary drive shaft extending outwardly from one end of the handle and an on/off button for actuation of the motor. The brush head assembly is formed by a housing sleeve attachable at one end to the handle and journaling an interior brush drive shaft releasably engaged at one end to the motor drive shaft and secured at its opposite end to a brush head. For journaling the brush head, the sleeve defines an inwardly directed flange defining in turn an inner cylindrical bearing surface and an outer annular thrust shoulder. A brush head with bristles extending therefrom includes an integral shaft extending therefrom and loosely journaled in the sleeve. The brush head and shaft define an outer cylindrical journal bearing surface and an annular thrust bearing surface surrounding the brush head.

When the electric motor is turned on, the motor oscillates the drive shaft which in turn oscillates the brush head drive shaft and thereby the brush head and bristles. The user applies the bristles against the teeth to be cleaned applying the necessary pressure to ensure an effective cleaning operation. During the teeth cleaning operation, the brush head is under a slight load so that the brush head shaft and the brush drive shaft are slightly canted away from alignment with the longitudinal axis of the motor shaft, and the cylindrical journal bearing surfaces on the housing sleeve and the brush head drive shaft engage to journal the brush head in the sleeve.

For reducing vibratory noises resulting from the oscillation of the brush head in the housing sleeve and vibratory contact of the annular thrust bearing surfaces when the brush head is not under a brushing load, a soft resilient annular bushing is positioned between the brush head shoulder and the housing sleeve end thrust surface, and defines circumferentially spaced prongs at its inner periphery separated by notches or slots. The prongs are sufficiently flexible to allow the cylindrical journal bearing surfaces of the housing sleeve and brush head to engage to support the oscillating brush head when a brushing load is placed on the bristles. Locking lugs on the housing sleeve flange engage with slots in the bushing to prevent both rotation and radial movement of the bushing relative to the housing sleeve.

BRIEF DESCRIPTION OF THE DRAWINGS

FIG. 1 is a perspective view of an electric motor powered toothbrush with a brush head assembly embodying the present invention.

FIG. 2 is an enlarged exploded view of the brush head assembly shown in FIG. 1.

FIG. 6 is a section taken substantially in the plane of line 6—6 on FIG. 3.

FIG. 7 is a section view taken substantially in the plane of line 7—7 of FIG. 5.

FIG. 8 is an enlarged, partial section view taken substantially in the plane of line 8—8 on FIG. 6.

FIG. 9 is an enlarged partial section view taken substantially in the plane of line 9—9 on FIG. 6.

DETAILED DESCRIPTION OF THE INVENTION

Figure 3:
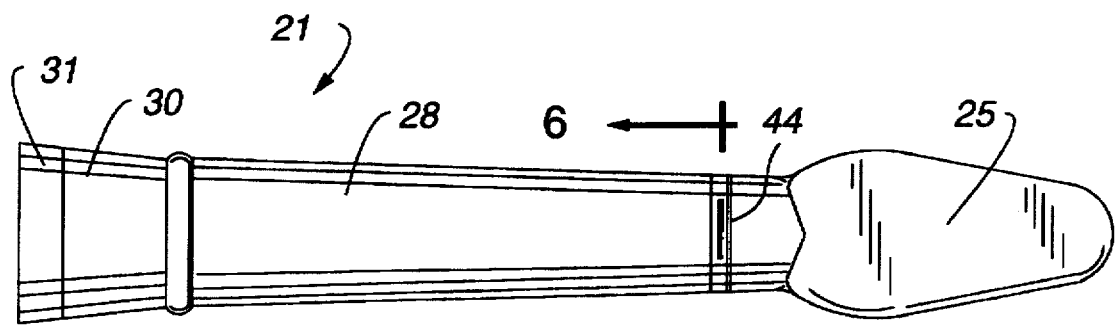
FIG. 3 is a plan view of the brush head assembly shown in FIG. 1.

The present invention is embodied in an electric toothbrush 20 incorporating an improved releasably attachable reduced noise brush head assembly 21 (FIG. 1). The electric toothbrush includes a handle 22 enclosing an electrically powered motor driven oscillating drive mechanism (not shown) having a primary drive shaft (not shown) which extends outwardly from one end of the handle 22. A finger actuated on/off switch 24 on the handle actuates the drive mechanism. The primary drive shaft is releasably coupled or splined to the brush head assembly 21 for oscillating a brush head 25 and bristles 26 carried thereby. In use, the user operates the electric toothbrush 20 by actuating the drive mechanism with the switch 24 to turn on the motor which oscillates the main drive shaft and thereby the brush head bristles. The user then positions the oscillating bristles 26 against the user's teeth and gums, and by applying some pressure or load, effects an efficient cleaning process. Any appropriate bristle configuration may be utilized. Accordingly, the bristles are shown generally schematically in the drawings.

Figure 4:
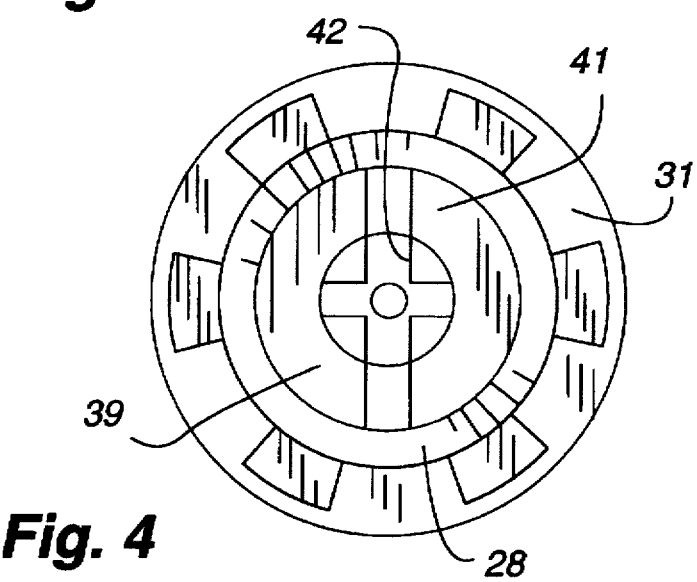
FIG. 4 is an enlarged left end view of the brush head assembly shown in FIG. 3.
Figure 5:
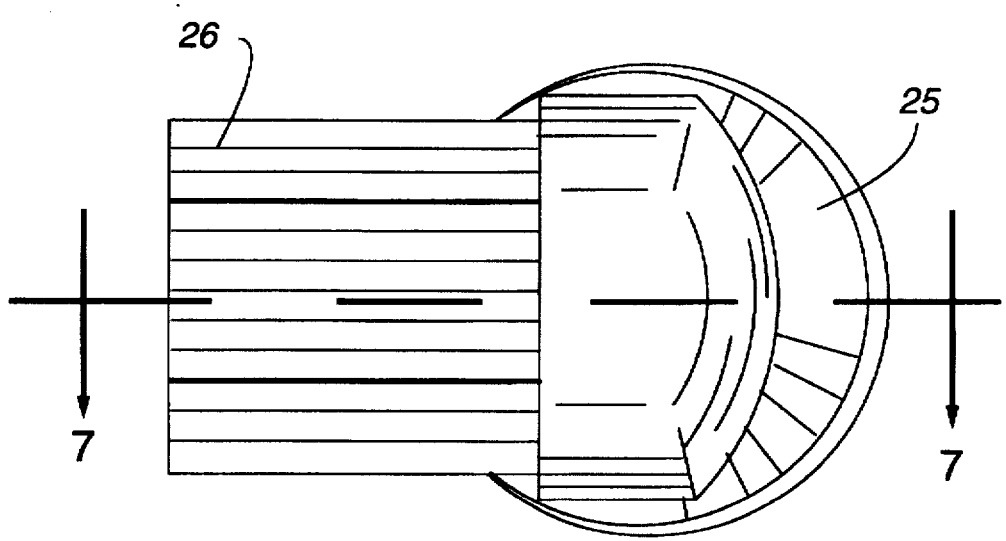
FIG. 5 is an enlarged right end view of the brush head assembly shown in FIG. 3.

The brush head assembly 21 (FIGS. 2–6) embodying the present invention is releasably attachable to the handle 22 in operative engagement with the oscillating primary drive shaft and is formed by an elongated housing sleeve 28 which may be tapered to define a larger end 30 and a smaller end 32 and a bore 29 therethrough (FIG. 7). At its larger end 30, the housing 28 is provided with a flexible seal ring 31 frictionally attachable to a mating annular rib (not shown) on the toothbrush housing 22. For journaling the brush head 25 for oscillating movement about the longitudinal axis of the motor drive shaft and brush head assembly, the housing 28 defines at its smaller end 32 an inwardly directed flange 34 defining an inner cylindrical bearing surface 35. The brush head 25 defines an axially extending shaft 36 having an external cylindrical journal bearing surface 38 which slidingly coacts with the internal cylindrical bearing surface 35 of the outer housing sleeve 28 to journal the brush head 25 for oscillatory movement about the longitudinal axis of the assembly when the brush head is under a load normal to its axis of oscillation. The brush head shaft may be a stub shaft as shown, or any appropriate shaft integral with or secured to the brush head.

In order to provide a driving connection between the motor drive shaft (not shown) and the brush head shaft 36, a brush drive shaft 39 is housed within the bore 29 of the housing sleeve 28 and secured or bonded at one end 40 to the stub shaft 36 of the brush head 25. The brush drive shaft 39 is preferably tapered for strength and rigidity. At its opposite end 41, the brush drive shaft 39 defines splines 42 adapted for releasable engagement with a splined end (not shown) of the motor drive shaft (not shown).

For reducing the amount of vibratory noise associated with the oscillation of the brush head 25 by the drive mechanism, a soft resilient annular bushing 44 is positioned between the outer annular end thrust surface 45 of the housing sleeve flange 34 and a thrust shoulder 46 defined on the brush head 25 around the brush head shaft 36 (FIGS. 7-9).

To support the brush head shaft while not interfering with or damping the oscillating motion thereof, the inner diameter of the annular bushing 44 defines an inner surface 48 of approximately the same diameter as, and preferably not smaller than, the external bearing surface 38 of the stub shaft 36. The bushing defines a plurality of spaced radial prongs 50 and intermediate notches or slots 51. To preclude the annular bushing 44 from rotating relative to the housing sleeve 28, and from moving radially relative to the housing sleeve 28 and the internal cylindrical bearing surface 35 defined therein, the sleeve is provided with a plurality of axially extending lugs 52 received in the radial notches 51 defined at the internal circumference of the annular bushing 44. An annular undercut or recess 54 is desirably formed in the shoulder 55 of the brush head defining the annular thrust surface 46 to receive the lugs 50 and thereby securely position the bushing between the brush head and the housing sleeve 28.

The radial prongs 52 are rounded at their innermost radial ends (as shown in FIG. 6) and define an internal cylinder having a diameter approximately equal to or greater than the external diameter of the stub shaft bearing surface 38. The bushing prongs, being precluded from rotary movement, support the brush head and brush drive shaft 39 for oscillating motion when the brush head 25 is not under a load normal to the axis of oscillation but, being resilient, are compressed radially and do not interfere with the journaling of the brush head shaft 36 in the housing sleeve 28 upon journaling engagement of the shaft cylindrical bearing surface 38 with the inner cylindrical bearing surface 35 of the sleeve flange 32 when the brush head is under a transverse load. The brush head remains free to oscillate at the desired frequency and the oscillatory motion is not damped when the brush head is under a brushing load.

The annular bushing 44 may be formed of any appropriate resilient material, such as a thermoplastic elastomer. The material must be soft and resilient enough to deform when the brush head is under a transverse load to allow the brush head shaft to journal in the housing sleeve without damping its oscillation, yet firm enough to journal the brush head shaft when no load is applied to the brush head. In other words, the bushing is stiff enough to resist unloaded vibrations, but soft enough to distort under load. It has been determined that an elastomer having a durometer of approximately 80 Shore A is preferable for the bushing, although other durometer elastomers can be expected to work as well. Lubricants may be added if desired. With this structure, not only is the oscillatory motion of the brush head not damped, the vibratory noises or rattles resulting from oscillatory contact between the brush head and the tubular housing are minimized when the electric tooth brush is "on" but no load is applied to the brush head.

While an illustrative embodiment of the present invention has been shown in the drawings and described above in considerable detail, it should be understood that there is no intention to limit the invention to the specific forms disclosed. On the contrary, the intention is to cover all modifications, alternatives, equivalents and uses falling within the spirit and scope of the invention as expressed in the appended claims.

What is claimed is:

1. A brush head assembly for a motor driven toothbrush including an elongated handle, said assembly comprising a housing sleeve attachable at one end to said handle, said sleeve having a second end defining an annular end surface and inner cylindrical journal bearing surface, a brush head including a brush head shaft journaled in said second sleeve end and defining an annular shoulder juxtaposed with said annular end surface of said sleeve and an external cylindrical journal bearing surface juxtaposed with said inner cylindrical journal bearing surface, and a resilient annular bushing positioned between said brush head shoulder and said housing sleeve end surface and defining an internal cylindrical journal bearing surface slidingly engageable with said external bearing surface on said brush head shaft.

2. A brush head assembly as defined in claim 1 wherein said bushing defines an inner periphery, and a plurality of radial prongs and intermediate radial notches are formed at said inner periphery, the inner radial end of said prongs defining said internal cylindrical journal bearing surface.

3. A brush head assembly as defined in claim 2 further comprising a lug extending from said annular sleeve end surface engageable in said bushing notches for preventing rotation of said bushing relative to said housing sleeve.

4. A brush head assembly as defined in claim 2 further comprising a plurality of lugs extending from said annular sleeve end surface and engageable in said bushing notches for preventing rotation of said bushing relative to said housing sleeve.

5. A brush head assembly for a motor driven toothbrush including an elongated handle, said assembly comprising a housing sleeve attachable at one end to said handle, said sleeve having a second end defining an annular end surface and inner cylindrical journal bearing surface, a brush head including a brush head shaft journaled in said second sleeve end and defining an annular shoulder juxtaposed with said annular end surface of said sleeve and an external cylindrical journal bearing surface juxtaposed with said inner cylindrical journal bearing surface, and a resilient annular bushing positioned between said brush head shoulder and said sleeve end surface, said bushing defining an inner periphery, and a plurality of radial prongs and intermediate radial notches formed at said inner periphery, the inner radial ends of said prongs being rounded and defining internal journal bearing surfaces slidingly engageable with said external bearing surface on said brush head shaft for journaling said brush head shaft when said brush head is not loaded.

6. A brush head assembly as defined in claim 5 further comprising a plurality of lugs extending from said annular sleeve end surface and engageable in said bushing notches for preventing rotation of said bushing relative to said housing sleeve.

7. A head assembly for a motor driven device including a handle, said assembly comprising a sleeve attachable at one end to said handle, said sleeve having a second end defining an annular end surface and inner cylindrical journal bearing surface, a head including a shaft journaled in said second sleeve end and defining an annular shoulder juxtaposed with said annular end surface of said sleeve and an external cylindrical journal bearing surface juxtaposed with said inner cylindrical journal bearing surface, and a resilient annular bushing positioned between said head shoulder and said sleeve end surface and defining an internal journal bearing surface slidingly engageable with said external bearing surface on said shaft.

8. A head assembly as defined in claim 7 wherein said bushing defines an inner periphery, with a plurality of radial prongs and intermediate radial notches formed at said inner periphery, the inner radial ends of said prongs defining said internal journal bearing surface.

9. A head assembly as defined in claim 8 further comprising a lug extending from said annular sleeve end surface engageable in said bushing notches for preventing rotation of said bushing relative to said sleeve.

10. A head assembly as defined in claim 8 further comprising a plurality of lugs extending from said annular sleeve end surface and engageable in said bushing notches for preventing rotation of said bushing relative to said sleeve.

11. A brush head assembly for a motor driven toothbrush including an elongated handle, said brush head assembly comprising a housing sleeve attachable at one end to said handle, a brush head, means journaling said brush head in said sleeve for oscillatory motion, and means for reducing vibratory noises when said brush head is not under a brushing load while being oscillated by said motion.

12. A brush head assembly as defined in claim 11 wherein said reducing means comprises a resilient bushing interposed between said brush head and said sleeve.

13. A brush head assembly as defined in claim 12 further comprising means for restraining said bushing against rotation relative to said sleeve.

* * * * *